United States Patent [19]

Caspari et al.

[11] Patent Number: 4,634,541

[45] Date of Patent: Jan. 6, 1987

[54] COLOR STABILIZERS FOR ZINC DITHIOPHOSPHATES

[75] Inventors: Gunter Caspari, Wheaton; Joseph J. Valcho, Naperville, both of Ill.

[73] Assignee: Standard Oil Company, Chicago, Ill.

[21] Appl. No.: 695,563

[22] Filed: Jan. 28, 1985

[51] Int. Cl.$^4$ .......................................... C10M 137/14
[52] U.S. Cl. ............................... 252/32.7 E; 252/46.6
[58] Field of Search .......................... 252/32.7 E, 46.6

[56] References Cited

U.S. PATENT DOCUMENTS

| 3,190,833 | 6/1965 | Rhodes | 252/32.7 E |
| 3,360,463 | 12/1967 | Jacques et al. | 252/32.7 E |
| 4,263,150 | 4/1981 | Clason et al. | 252/32.7 E |

*Primary Examiner*—Jacqueline V. Howard
*Attorney, Agent, or Firm*—William C. Clarke; William T. McClain; William H. Magidson

[57] ABSTRACT

A small amount of hydrogen sulfide, an olefin, a mercaptan, an epoxide, a phosphite or a phosphine are added to a zinc dialkyldithiophosphate salt to decrease the rate of color generation upon storage and/or exposure to heat.

11 Claims, No Drawings

COLOR STABILIZERS FOR ZINC DITHIOPHOSPHATES

FIELD OF THE INVENTION

The field of this invention relates to a composition comprising a lubricant oil additive useful as an inhibitor of engine wear, lubricant oxidation and engine part corrosion. More particularly, this invention relates to a composition of a lubricating oil additive comprising an oil-soluble zinc dialkyldithiophosphate wherein addition of small amounts of a compound selected from the group consisting of olefins, mercaptans, epoxides, phosphites, and phosphines decreases the rate of oxidation of the zinc dialkyldithiophosphate under conditions of heat and/or prolonged storage. The decreased rate of oxidation decreases the rate of color generation or color formation.

It is an object of this invention to provide a lubricant composition comprising a wear inhibitor which has increased oxidative stability as an additive in a lubricating oil composition and good color stabilization in storage at elevated temperatures.

It is an object of this invention to provide a lubricant composition comprising a wear inhibitor mixture which has improved oxidative stability in a lubricating oil composition wherein the wear inhibitor comprises an oil-soluble zinc dialkyldithiophosphate.

It is an object of this invention to provide a process for the preparation of a wear inhibitor mixture which demonstrates improved color stability at elevated temperatures.

It is an object of this invention to provide a process for preparation of a lubricating oil composition which comprises an oil-soluble zinc dialkyldithiophosphate and demonstrates improved color stability at elevated temperatures.

These and other objects will become apparent from the description given hereafter.

BACKGROUND OF THE INVENTION

Oil-soluble zinc dithiophosphates are used as compounding agents or additives in lubricating oils to inhibit engine wear, to inhibit oxidation of the lubrication oil, and to inhibit engine part corrosion. It is highly desirable for such oil-soluble zinc dialkyldithiophosphates to provide the aforesaid properties to the lubricating oil without affecting the appearance characteristics of the formulated lubricant composition even though the performance characteristics of the lubricant composition may not be affected noticeably.

As is well known, oil-soluble zinc dialkyldithiophosphates are conventionally prepared by reacting monohydric alcohols or phenols with phosphorus pentasulfide, usually in a mole ratio of 4:1, alcohol to phosphorus pentasulfide, in the presence of a diluent oil at a temperature within the range of from about 70° C. to about 135° C. to form partial esters of dithiophosphoric acid, a green odoriferous liquid. The so-obtained partial esters are then neutralized with zinc oxide at a temperature within the range of from about 70° C. to about 135° C. to form a zinc dialkyldithiophosphate, typically a light yellow liquid.

It has been found that, upon storage, the zinc dialkyldithiophosphate prepared as described often will acquire a dark objectionable color, often of a brownish hue. The dark color is objectionable as it affects the marketing of the zinc dialkyldithiophosphates. The dark product has been considered as inferior to product of a light color.

It has long been known that the metal salts of partial esters of dithiophosphoric acids can be decolorized by incorporation of a small amount of a trialkylolamine whose alkylol groups contain 1 to 4 carbon atoms each. U.S. Pat. No. 2,983,742 teaches that excellent results have been obtained with triethanolamine but other amines of the class disclosed can be used. Amounts can be used of from 0.25 to 1.0 percent by weight. U.S. Pat. No. 3,361,668 teaches and claims a lubricating composition containing light-colored metal phosphorodithioates wherein the said phosphorodithioate is prepared by reacting phosphorus pentasulfide with a mixture of from about 95% to 99.95% by weight of a monohydroxy alcohol or phenol having from 1 to 30 carbon atoms and from about 0.05% to 5.0% by weight of an alkyl amine, cycloalkylamine or heterocyclic amine having up to about 20 carbon atoms. In an alternative procedure, the phosphorodithioic acid diester is first prepared and a small amount of a suitable amine is then added.

In the prior art, it has been postulated that the cause of the dark color in metal salts of dithiophosphate esters is the presence of traces of heavy metals, principally iron, in the phosphorus pentasulfides. U.S. Pat. No. 2,983,742, Boba, et al, considers that addition of a trialkylolamine forms complexes with traces of the heavy metal compounds in the dithiophosphate esster salt that are more stable than the uncomplexed metal compounds. However, Boba, et al, U.S. Pat. No. 2,983,742 indicate this postulate is somewhat negatived by the fact that other agents capable of forming complexes with heavy metal compounds do not produce equivalent results. Wiese, U.S. Pat. No. 3,361,668, teaches that commercially prepared phosphorodithioic acid diesters are sufficiently strong acids to be corrosive to metals and the use of special corrosion-resistant equipment is generally required in their manufacture. Wiese U.S. Pat. No. 3,361,668 teaches that the corrosiveness of the phosphorodithioic acid esters upon mild steel is shown to be reduced in the presence of an amine-reacted product of a phosphorodithioic acid ester. Wiese U.S. Pat. No. 3,361,668 accordingly teaches that the amine-reacted product of a phosphorodithioic acid is less reactive to iron compounds and retains its light color as prepared.

It has now been found unexpectedly that acid salts comprising zinc dialkyldithiophosphates substantially retain their original light color despite exposure to elevated temperatures for prolonged periods of time upon the addition of color stabilizers in an amount not greater than 1.0 (wt)% of the zinc dialkyldithiophosphate metal salt in concentrations of from 0.0001 to 0.5 mole of stabilizer per mole of zinc dialkyldithiophosphate metal salt. A preferred range is 0.002 to 0.05 mole of stabilizer per mole of zinc dialkyldithiophosphate. The color stabilizers are added after the dialkyldithiophosphoric acid diester is neutralized with zinc oxide to prepare the zinc dialkyldithiophosphate. Some of the color stabilizers are preferably added to the dialkyl dithiophosphoric acid diester after it is neutralized with zinc oxide. The color stabilizers comprise hydrogen sulfide, olefins, mercaptans, epoxides, phosphites, and phosphones.

Although the mechanism has not been definitely established by which the color stabilizers cause the zinc dialkyldithiophosphate to retain a light color, it is believed that the addition of the aforementioned color stabilizers decreases the rate of oxidation of the zinc dialkyldithiophosphate under conditions of heat and/or prolonged storage; nor has the darkening of the zinc dialkyldithiophosphate been definitely established as having been caused by the presence of oxygen and consequent oxidation of the dithiophosphate ester. It is also considered that traces of other compounds may be present which react with zinc dialkyldithiophosphate to cause a darkening of the ester.

SUMMARY OF THE INVENTION

A small amount of hydrogen sulfide, an olefin, a mercaptan, an epoxide, a phosphite or a phosphine is added to a zinc dialkyldithiophosphate salt to decrease the rate of color formation or color generation upon storage and/or exposure to heat.

DETAIL OF THE INVENTION

O,O'-phosphorodithioic acid diesters are manufactured by reacting about 4 equivalents of an organic monohydroxy compound, e.g., an alcohol or a phenol with one mole of phosphorus pentasulfide at temperatures of from about 70° C. to about 135° C. with the evolution of hydrogen sulfide as illustrated by the following equation:

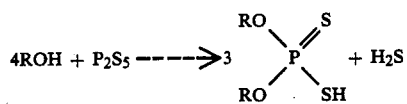

The oil-soluble metal phosphorodithioate diester salts are usually manufactured by neutralizing the phosphorodithioic acid diester with a basically reacting metal compound, preferably the oxide, frequently with a small amount of water added, at temperatures of from about 50° C. to about 150° C.

A phosphorodithioic acid diester is usually assumed to have the structure shown in the above equation wherein the thiol group attached to the phosphorus atom accounts for its relatively strong acidic character. In addition, unless the alcohols used are anhydrous, traces of water which are present in the reaction mixture react with the phosphorus pentasulfide to cause the formation of small amounts of monoesters of phosphorodithioic acid or phosphoromonothioic acid and even some unesterified phosphorus and sulfur-containing acids.

Suitable monohydroxy organic compounds useful in the preparation of the improved O,O'-diesters of phosphorodithioic acid include alcohols, phenols, and alkyl phenols, including their substituted derivatives, e.g., nitro-, haloalkoxy-, hydroxy-, carboxy-, etc. Suitable alcohols include, for example, methanol, ethanol, n-propanol, isopropanol, n-butanol, 2-butanol, 2-methylpropanol, n-pentanol, 2-pentanol, 3-pentanol, 2-methylbutanol, 3-methyl-2-pentanol, n-hexanol, 2-hexanol, 3-hexanol, 2-methyl-2-pentanol, 4-methyl-3-pentanol, cyclohexanol, chlorocyclohexanol, methylcyclohexanol, heptanol, 2-ethylhexanol, n-octanol, 2,2-dimethyloctanol, nonanol, dodecanol, octadecanol, eicosanol, etc. The phenols suitable for the purposes of this invention include alkyl phenols and substituted phenols, e.g., phenol, chlorophenol, bromophenol, nitrophenol, methoxyphenol, cresol, propylphenol, butylphenol, amylphenol, heptylphenol, octylphenol, nonylphenol, octadecylphenol, etc. Ordinarily, the monohydroxy organic compounds suitable for purposes of this invention may have from 1 to about 30 carbon atoms. Mixtures of monohydroxy organic compounds can also be used without penalty to produce oil-soluble metal salts. Alcohols most frequently used are isobutanol, isoamyl, alcohol, isooctanol, 2-propanol, 4-methyl-2-pentanol, capryl alcohol, and nonylphenol.

The color stabilizers suitable for use in this invention for preparing the improved zinc dialkyldithiophosphate include olefins, mercaptans, epoxides, phosphites, and phosphines. Olefinic compounds useful as color stabilizers can be selected from a large variety of compounds containing olefinic double bonds such as alpha olefins of 2 to 100 carbon atoms, cyclic olefins such as cyclohexene, dicyclopentadiene, terpenenes, and olefinic compounds with functional groups such as allyl and oleyl alcohol, acrylic acid, and methacrylic acid and their esters, oleic acid, styrene, vinylethers, vinylesters, and vnylpyrrolidone. Mercaptans can be selected from primary, secondary, or tertiary mercaptans of 4 to 40 carbon atoms; $H_2S$ can also be used as a color stabilizer. Epoxides are selected from compounds with 2 to 100 carbon atoms, such as epoxybutane or epoxidized soybean oil. Trialkyl or triarylphosphites can be selected from compounds of the formula $(RO)_3P$ where R is an alkyl group or a phenyl or substituted phenyl group of from 1 to 30 carbon atoms. Trialkylphosphines have the general formula $R_3P$ where R is an alkyl group of from 1 to 20 carbon atoms.

The proposed color stabilizers are usually added after the dialkyl dithiophosphoric acid is neutralized with zinc oxide. Some of the stabilizers such as phosphites, phosphines, or mercaptans can be added before neutralization with zinc oxide is completed.

The color stabilizing additive can be added in concentrations ranging from 0.0001 to 0.5 mole of stabilizer per mole of zinc dialkyldithiophosphate (ZnDTP). A preferred range is 0.002 to 0.05 mole of stabilizer per mole of zinc dialkyldithiophosphate (ZnDTP).

The following examples are illustrative of typical compositions of the instant invention and the results obtainable therefrom.

EXAMPLE I

A sample of 50 g ZnDTP was added to a bottle of the dimensions 37×155 mm equipped with a screw cap. Color stabilizers were added and mixed with the ZnDTP. After storing the bottles in an oven, the ASTM color of the test samples was measured in a standard apparatus for measuring ASTM color as described in ASTM D-1500. The ASTM procedure uses a color scale ranging from 0.5 to 8.0 color units, 0.5 being light and 8.0 dark in color.

A ZnDTP composed of 50 mole % 2-propyl and 50 mole % 4-methyl-2-pentyl alkyl groups was tested; elemental analysis of ZnDTP was: Zn—8.96%, P—8.12%, storage temperature 75° C.

| | | ASTM D-1500 Color | |
|---|---|---|---|
| Additive | % (wt.) | 0 Hrs. | 465 Hrs. |
| 1. No Additive (Control) | — | 2.0 | 6.0 |
| 2. d-Limonene | 0.30 | 2.0 | 3.0 |
| 3. Dipentene[1] | 0.32 | 2.0 | 3.0 |
| 4. $C_{15-20}$ alpha Olefin | 0.30 | 2.0 | 3.0 |
| 5. Allyl Alcohol | 0.24 | 2.0 | 2.0 |
| 6. Dicyclopentadiene | 0.24 | 2.0 | 3.0 |
| 7. alpha-Methyl Styrene | 0.30 | 2.0 | 3.0 |

-continued

| Additive | % (wt.) | ASTM D-1500 Color | |
|---|---|---|---|
| | | 0 Hrs. | 465 Hrs. |
| 8. Styrene | 0.44 | 2.0 | 4.5 |
| 9. Oleyl Alcohol | 0.32 | 2.0 | 4.0 |
| 10. 1-Dodecylmercaptan | 0.42 | 2.0 | 3.5 |
| 11. Tertiary Dodecylmercaptan | 0.42 | 2.0 | 3.0 |
| 12. Needox 1114[2] | 0.61 | 2.0 | 3.5 |
| 13. Tri-n-Butylphosphine | 0.36 | 2.0 | 3.0 |
| 14. Hydrogen Sulfide[3] | saturated | 2.0 | 3.5 |

[1]Dipentene-122 (Hercules Inc., Wilmington, Delaware)
[2]Needox 1114 - Epoxide of $C_{11-14}$ (Ashland Chemical Co., Industrial Chemicals and Solvents Div., Columbus, Ohio)
[3]$H_2S$ was sparged through sample before oven storage.

EXAMPLE II

A storage test with ZnDTP of a test series was carried out at 93° C.

| Additive | % (wt.) | ASTM D-1500 Color | |
|---|---|---|---|
| | | 0 Hrs. | 72 Hrs. |
| 15. No Additive (Control) | — | 2.0 | 6.5 |
| 16. Epoxybutane | 0.62 | 2.0 | 3.0 |
| 17. Triethylphosphite | 0.62 | 2.0 | 2.0 |
| 18. d-Limonene | 0.30 | 2.0 | 3.0 |

EXAMPLE III

A ZnDTP composed of 65 mole % isobutyl, 25 mole % isoamyl, and 10 mole % isooctyl alkyl groups was tested; elemental analysis of ZnDTP was: Zn—8.75%, P—7.76%, storage temperature—93° C.

| Additive | % (wt.) | ASTM D-1500 Color | |
|---|---|---|---|
| | | 0 Hrs. | 72 Hrs. |
| 19. No Additive (Control) | — | 3.0 | 7.5 |
| 20. $C_{15-20}$ alpha Olefin | 0.57 | 3.0 | 3.5 |
| 21. 1—Dodecylmercaptan | 0.62 | 3.0 | 4.0 |
| 22. Epoxybutane | 0.53 | 3.0 | 3.5 |
| 23. Triethylphosphite | 0.61 | 3.0 | 3.0 |
| 24. Tri-n-Butylphosphine | 0.52 | 3.0 | 3.0 |

EXAMPLE IV

A ZnDTP composed of 50 mole % 2-propyl and 50 mole % isooctyl alkyl groups was stored at 93° C.; elemental composition of ZnDTP was: Zn—8.06%, P—7.13%.

| Additive | % (wt.) | ASTM D-1500 Color | |
|---|---|---|---|
| | | 0 Hrs. | 72 Hrs. |
| 25. No Additive (Control) | — | 2.0 | 7.5 |
| 26. $C_{16}$ alpha Olefin | 0.31 | 2.0 | 4.0 |
| 27. Allyl Alcohol | 0.46 | 2.0 | 3.0 |
| 28. Epoxybutane | 0.54 | 2.0 | 3.5 |
| 29. Triethylphosphite | 0.30 | 2.0 | 3.5 |
| 30. Tri-n-Butylphosphine | 0.29 | 2.0 | 2.5 |
| 31. 1—Dodecylmercaptan | 0.61 | 2.0 | 3.5 |

EXAMPLE V

In the procedure of Example I, amine compounds were added to samples of ZnDTP and stored at 200° F. (93° C.) for 46 and 70 hours. Colors were determined according to ASTM D-1500. Results are in the following table.

| Darkening of ZnDTP in the Presence of Amine at 93° C. | | | | |
|---|---|---|---|---|
| | | ASTM D-1500 Color | | |
| | | 0 Hrs. | 46 Hrs. | 70 Hrs. |
| Control (No Amines) | | 2.0 | 5.5 | 6.5 |
| % (wt) | Amine | | | |
| 0.30 | 2-Ethyl-1-Hexylamine | 2.0 | 5.5 | 6.5 |
| 0.42 | 2-(2-Aminoethyl-amine) ethanol | 2.0 | 5.5 | 6.5 |
| 0.34 | Aniline | 2.0 | 6.5 | 7.5 |
| 0.36 | Diethylamine | 2.0 | 7.0 | 7.5 |
| 0.36 | 2,4-Lutidine | 2.0 | 5.5 | 6.5 |
| 0.36 | Picoline | 2.0 | 5.5 | 6.5 |
| 0.34 | N,N'—Dimethylaniline | 2.0 | 6.0 | 6.5 |
| 0.44 | Triethanolamine | 2.0 | 5.0* | 5.5* |

Notes: *Deposits formed

What is claimed is:

1. A process comprising incorporating in a metal salt of an ester of dithiophosphoric acid a small amount, sufficient to decrease the rate of color generation in the product, of a color stabilizer compound selected from the group consisting of hydrogen sulfide, an olefin of from 2 to 100 carbon atoms, a mercaptan of from 4 to 40 carbon atoms, and trialkylphosphines of the formula $R^1_3P$ where $R^1$ is an alkyl group of 1 to 20 carbon atoms, said small amount not being greater than about 1.0 (wt)% of the weight of said metal salt.

2. The process of claim 1 wherein said olefin is selected from the group consisting of an alpha olefin is from 15 to 20 carbon atoms, dipentene, styrene, alpha methyl styrene, oleyl alcohol, d-limonene, dicyclopentadiene and allyl alcohol.

3. The process of claim 1 wherein said mercaptan is selected from the group consisting of 1-dodecylmercaptan and tertiary dodecylmercaptan.

4. The process of claim 1 wherein said phosphine is tri-n-butylphosphine.

5. The process of claim 1 wherein said metal salt of an ester of dithiophosphoric acid is a zinc dialkyldithiophosphate.

6. The process of claim 1 wherein said small amount is from 0.0001 to 0.5 mole of said color stabilizer compound per mole of said metal salt of an ester of dithiophosphoric acid.

7. A composition comprising a major portion of a metal salt of an ester of dithiophosphoric acid and a small amount of a color stabilizer compound selected from the group consisting of hydrogen sulfide, an olefin of from 2 to 100 carbon atoms, a mercaptan of from 2 to 100 carbon atoms, and trialkylphosphines of the formula $R^1_2P$ where $R^1$ is an alkyl group of from 1 to 20 carbon atoms, said small amount being not greater than about 1.0 (wt%) of the weight of said metal salt.

8. A composition of claim 7 wherein said metal salt of an ester of dithiophosphoric acid is a zinc dialkyldithiophosphate.

9. The composition of claim 7 wherein said olefin is selected from the group consisting of an alpha olefin of from 15 to 20 carbon atoms, dipentene, styrene, alpha methyl styrene, oleyl alcohol, d-limonene, dicyclopentadiene and allyl alcohol.

10. The composition of claim 7 wherein said mercaptan is selected from the group consisting of 1-dodecylmercaptan and tertiary dodecylmercaptan.

11. The composition of claim 7 wherein said phosphine is tri-n-butylphosphine.

* * * * *